(12) United States Patent
Laurencin et al.

(10) Patent No.: US 8,603,968 B2
(45) Date of Patent: Dec. 10, 2013

(54) CYCLIC PEPTIDES COMPRISING AT LEAST ONE AZA-β3-AMINOACYL RESIDUE AND THEIR USES

(75) Inventors: Mathieu Laurencin, Rennes (FR); Céline Zatylny-Gaudin, Bretteville sur Odon (FR); Joël Henry, Bayeux (FR); Michéle Baudy Floc'H, Rennes (FR)

(73) Assignees: Centre National de la Recherche Scientifique, Paris (FR); Universite de Rennes I, Rennes (FR)

( * ) Notice: Subject to any disclaimer, the term of this patent is extended or adjusted under 35 U.S.C. 154(b) by 625 days.

(21) Appl. No.: 12/682,129

(22) PCT Filed: Oct. 8, 2008

(86) PCT No.: PCT/FR2008/001403
§ 371 (c)(1),
(2), (4) Date: Jul. 26, 2010

(87) PCT Pub. No.: WO2009/083633
PCT Pub. Date: Jul. 9, 2009

(65) Prior Publication Data
US 2010/0305027 A1 Dec. 2, 2010

(30) Foreign Application Priority Data
Oct. 10, 2007 (FR) ...................... 07 07108

(51) Int. Cl.
*A61K 38/04* (2006.01)
*A01N 37/18* (2006.01)

(52) U.S. Cl.
USPC ............................. 514/2.8; 514/1.1; 514/2.9

(58) Field of Classification Search
None
See application file for complete search history.

(56) References Cited

FOREIGN PATENT DOCUMENTS

| FR | 2 922 211 A1 | 4/2009 |
| FR | 2 925 502 A1 | 6/2009 |
| WO | 2004/111086 A | 12/2004 |

OTHER PUBLICATIONS

Chapman et al. "In Search of the Holy Grail of Antifungal Therapy." Transactions of the American Clinical and Climatological Association, Vol. 119, 2008, pp. 197-216.*
Lembo et al. "Nanoparticulate delivery systems for antiviral drugs." Antiviral Chemistry & Chemotherapy. vol. 21, pp. 53-70. 2010.*
Sexana et al. "Emerging Trends, Challenges and Prospects in Antiviral Therapeutics and Drug Development for Infectious Diseases" Electronic Journal of Biology, 2010, vol. 6(2): 26-31.*
Busnel 0 et al. : "Structure-activity studies of cyclic aza-beta-3-RGD peptide analogs", Journal of Peptide Science, vol. 12, No. Suppl. S, Sep. 2006, p. 169, XP009099748.
Le Grel Philippe et al.: "Aza-beta3-cyclohexapeptides: pseudopeptidic macrocycles with interesting conformational and configurational properties slow pyramidal nitrogen inversion in 24-membered rings" The Journal of Organic Chemistry, Jul. 21, 2006, pp. 5638-5645, vol. 71, No. 15, XP009096823.
Lenman, Morag M. et al.: "Synthesis of fused 1,2,5-triazepine-I,5-diones and some N2- and N3-substituted derivatives: potential conformational mimetics for cis-peptidyl prolinamides", Journal of the Chemical Society, Perkin Transactions 1: Organic and Bio-Organic Chemistry, 1997, pp. 2297-2311, No. 16, XP009099828.
Legrand Baptiste et al.: "Auto-assembling antimicrobial cyclic pseudopeptides including aza-beta(3)-amino acids", Journal of Peptide Science, Aug. 2008, p. 60,vol. 14, No. 8, Suppl. S, Aug. 2008, XP9119061.
International Search Report in Corresponding Application No. PCT/FR2008/001403 Dated Jul. 8, 2009.

* cited by examiner

*Primary Examiner* — Cecilia J Tsang
*Assistant Examiner* — Randall L Beane
(74) *Attorney, Agent, or Firm* — Young & Thompson

(57) ABSTRACT

Cyclic peptides having a random alternation of L-α-aminoacyl residues and aza-β³-aminoacyl residues and their uses.

15 Claims, 9 Drawing Sheets

FIGURE 2

Minimum inhibitory concentrations (MIC) of bacterial proliferation expressed in µg/mL

A

|  | NafNaf | TrypTryp | 4KW | 3K2 | 3KW |
|---|---|---|---|---|---|
| *Bacillus megaterium* (Gram+ non-pathogenic) | 5_10 | 20_40 | 80_160 | 40_80 | 160_320 |
| *Staphylococcus aureus* (Gram+ pathogenic) | 2.5_5 | 40_80 | 80_160 | 160_320 | NA |
| *Escherichia coli* (Gram- pathogenic) | 20_40 | 160_320 | NA | > 320 | NA |
| *Pseudomonas aeruginosa* (Gram- pathogenic) | 10_20 | 160_320 | 160_320 | > 320 | NA |
| *Salmonella typhimurium* (Gram- pathogenic) | 10_20 | 80_160 | NA | 160_320 | NA |
| *Klebsiella pneumoniae* (Gram- pathogenic) | 40_80 | > 320 | NA | NA | NA |

NA : no antimicrobial activity

Minimum bactericidal concentration (MBC) for the NafNaf peptide

B

| Bacteria | *Bacillus megaterium* | *Staphylococcus aureus* | *Escherichia coli* | *Salmonella typhimurium* |
|---|---|---|---|---|
| MBC (µg/mL) | < 40 | < 10 | < 80 | < 20 |

Effect of the NafNaf peptide on *Staphylococcus aureus*

Effect of the NafNaf peptide on *Salmonella typhimurium*

Haemolytic activity curve of the NafNaf cyclic pseudopeptide

Cytotoxicity of the NafNaf pseudopeptide on normal cells and cancer cells

FIGURE 7

Minimum inhibitory concentrations (MIC) of bacterial proliferation expressed in μM

| Pseudopeptide / Strain | NafNaf | 4Fluo1Naf | OctOct | Chado | FluoKil |
|---|---|---|---|---|---|
| Staphylococcus aureus[+] | 25 | 12.5 | 6.25 | 25 | 25 |
| Enterococcus faecalis[+] | 50 | 25 | 12.5 | 12.5 | 50 |
| Streptococcus equinus[+] | 6.25 | 6.25 | 6.25 | 12.5 | 6.25 |
| Listeria monocytogenes[+] | 12.5 | 6.25 | 3.12 | 12.5 | 6.25 |
| Bacillus megaterium[+] | 3.12 | 3.12 | 6.25 | 12.5 | 1.56 |
| Lactococcus gaviae[+] | 50 | 25 | 6.25 | 50 | 25 |
| Micrococcus luteus[+] | 3.12 | 3.12 | 3.12 | 12.5 | 3.12 |
| Escherichia Coli[-] | 50 | 25 | ND | ND | 25 |
| Pseudomonas Aeruginosa[-] | 50 | 25 | 25 | ND | 50 |
| Salmonella Enterica[-] | 50 | 50 | ND | ND | 50 |
| Klebsiella Oxytoca[-] | 50 | 25 | ND | ND | 25 |
| Enterobacter aerogenes[-] | 50 | 50 | ND | ND | 12.5 |
| Aeromonas Caviae[-] | ND | ND | ND | ND | ND |

Haemolytic activity of peptides according to the invention on sheep erythrocytes.

```
                              SEQUENCE LISTING

<160> NUMBER OF SEQ ID NOS: 25

<210> SEQ ID NO 1
<211> LENGTH: 6
<212> TYPE: PRT
<213> ORGANISM: Artificial Sequence
<220> FEATURE:
<223> OTHER INFORMATION: Cyclic peptide comprising three aza-B3-
      aminoacyle residues
<220> FEATURE:
<221> NAME/KEY: MISC_FEATURE
<222> LOCATION: (2)..(2)
<223> OTHER INFORMATION: Xaa1=aza3K
<220> FEATURE:
<221> NAME/KEY: MISC_FEATURE
<222> LOCATION: (4)..(4)
<223> OTHER INFORMATION: Xaa2=aza3(1)Nal
<220> FEATURE:
<221> NAME/KEY: MISC_FEATURE
<222> LOCATION: (6)..(6)
<223> OTHER INFORMATION: Xaa2=aza3(1)Nal

<400> SEQUENCE: 1

Leu Xaa Lys Xaa Leu Xaa
1               5

<210> SEQ ID NO 2
<211> LENGTH: 6
<212> TYPE: PRT
<213> ORGANISM: Artificial Sequence
<220> FEATURE:
<223> OTHER INFORMATION: Cyclic peptide containing three aza-B3-
      aminoacyle residues
<220> FEATURE:
<221> NAME/KEY: MISC_FEATURE
<222> LOCATION: (2)..(2)
<223> OTHER INFORMATION: Xaa1= aza3K
<220> FEATURE:
<221> NAME/KEY: MISC_FEATURE
<222> LOCATION: (4)..(4)
<223> OTHER INFORMATION: Xaa2= aza3Nal
<220> FEATURE:
<221> NAME/KEY: MISC_FEATURE
<222> LOCATION: (6)..(6)
<223> OTHER INFORMATION: Xaa3=aza3Nal

<400> SEQUENCE: 2

Lys Xaa Leu Xaa Leu Xaa
1               5

<210> SEQ ID NO 3
<211> LENGTH: 6
<212> TYPE: PRT
<213> ORGANISM: Artificial Sequence
<220> FEATURE:
<223> OTHER INFORMATION: Cyclic peptide comprising three aza-B3-
      aminoacyle residues
<220> FEATURE:
<221> NAME/KEY: MISC_FEATURE
<222> LOCATION: (2)..(2)
<223> OTHER INFORMATION: Xaa1=aza3K
<220> FEATURE:
<221> NAME/KEY: MISC_FEATURE
<222> LOCATION: (4)..(4)
<223> OTHER INFORMATION: Xaa2=aza3L
<220> FEATURE:
<221> NAME/KEY: MISC_FEATURE
<222> LOCATION: (6)..(6)
<223> OTHER INFORMATION: Xaa2=aza3L
```

-continued

```
<400> SEQUENCE: 3

Lys Xaa Trp Xaa Trp Xaa
1               5

<210> SEQ ID NO 4
<211> LENGTH: 6
<212> TYPE: PRT
<213> ORGANISM: Artificial Sequence
<220> FEATURE:
<223> OTHER INFORMATION: Cyclic peptide comprising three aza-B3-
      aminoacyle residues
<220> FEATURE:
<221> NAME/KEY: MISC_FEATURE
<222> LOCATION: (2)..(2)
<223> OTHER INFORMATION: Xaa1= aza3K
<220> FEATURE:
<221> NAME/KEY: MISC_FEATURE
<222> LOCATION: (4)..(4)
<223> OTHER INFORMATION: Xaa2=aza3L
<220> FEATURE:
<221> NAME/KEY: MISC_FEATURE
<222> LOCATION: (6)..(6)
<223> OTHER INFORMATION: Xaa3=aza3L

<400> SEQUENCE: 4

Lys Xaa Lys Xaa Trp Xaa
1               5

<210> SEQ ID NO 5
<211> LENGTH: 6
<212> TYPE: PRT
<213> ORGANISM: Artificial Sequence
<220> FEATURE:
<223> OTHER INFORMATION: Cyclic peptide comprising three aza-B3-
      aminoacyle residues
<220> FEATURE:
<221> NAME/KEY: MISC_FEATURE
<222> LOCATION: (2)..(2)
<223> OTHER INFORMATION: Xaa1=aza3K
<220> FEATURE:
<221> NAME/KEY: MISC_FEATURE
<222> LOCATION: (4)..(4)
<223> OTHER INFORMATION: Xaa2=aza3K
<220> FEATURE:
<221> NAME/KEY: MISC_FEATURE
<222> LOCATION: (6)..(6)
<223> OTHER INFORMATION: Xaa3=aza3L

<400> SEQUENCE: 5

Trp Xaa Lys Xaa Trp Xaa
1               5

<210> SEQ ID NO 6
<211> LENGTH: 6
<212> TYPE: PRT
<213> ORGANISM: Artificial Sequence
<220> FEATURE:
<223> OTHER INFORMATION: Cyclic peptide comprising three aza-B3-
      aminoacyle residues
<220> FEATURE:
<221> NAME/KEY: MISC_FEATURE
<222> LOCATION: (2)..(2)
<223> OTHER INFORMATION: Xaa1 = aza3K
<220> FEATURE:
<221> NAME/KEY: MISC_FEATURE
<222> LOCATION: (4)..(4)
<223> OTHER INFORMATION: Xaa2 = aza3K
<220> FEATURE:
<221> NAME/KEY: MISC_FEATURE
<222> LOCATION: (6)..(6)
<223> OTHER INFORMATION: Xaa3 = aza3(1)Nal

<400> SEQUENCE: 6
```

```
Lys Xaa Lys Xaa Trp Xaa
1               5
```

<210> SEQ ID NO 7
<211> LENGTH: 8
<212> TYPE: PRT
<213> ORGANISM: Artificial Sequence
<220> FEATURE:
<223> OTHER INFORMATION: Cyclic peptide comprising three aza-B3-
      aminoacyle residues
<220> FEATURE:
<221> NAME/KEY: MISC_FEATURE
<222> LOCATION: (2)..(2)
<223> OTHER INFORMATION: Xaa1 = aza3(1)Nal)
<220> FEATURE:
<221> NAME/KEY: MISC_FEATURE
<222> LOCATION: (4)..(4)
<223> OTHER INFORMATION: Xaa2 = aza3K
<220> FEATURE:
<221> NAME/KEY: MISC_FEATURE
<222> LOCATION: (6)..(6)
<223> OTHER INFORMATION: Xaa3 = aza3K
<220> FEATURE:
<221> NAME/KEY: MISC_FEATURE
<222> LOCATION: (8)..(8)
<223> OTHER INFORMATION: Xaa4 = aza3K

<400> SEQUENCE: 7

```
Ser Xaa Phe Xaa Thr Xaa Ser Xaa
1               5
```

<210> SEQ ID NO 8
<211> LENGTH: 6
<212> TYPE: PRT
<213> ORGANISM: Artificial Sequence
<220> FEATURE:
<223> OTHER INFORMATION: Cyclic peptide comprising three aza-B3-
      aminoacyle residues
<220> FEATURE:
<221> NAME/KEY: MISC_FEATURE
<222> LOCATION: (2)..(2)
<223> OTHER INFORMATION: Xaa1 = aza3R
<220> FEATURE:
<221> NAME/KEY: MISC_FEATURE
<222> LOCATION: (4)..(4)
<223> OTHER INFORMATION: Xaa2 = aza3(1)Nal
<220> FEATURE:
<221> NAME/KEY: MISC_FEATURE
<222> LOCATION: (6)..(6)
<223> OTHER INFORMATION: Xaa3 = aza3(1)Nal

<400> SEQUENCE: 8

```
Leu Xaa Arg Xaa Leu Xaa
1               5
```

<210> SEQ ID NO 9
<211> LENGTH: 6
<212> TYPE: PRT
<213> ORGANISM: Artificial Sequence
<220> FEATURE:
<223> OTHER INFORMATION: Cyclic peptide comprising four aza-B3-
      aminoacyle residues
<220> FEATURE:
<221> NAME/KEY: MISC_FEATURE
<222> LOCATION: (2)..(2)
<223> OTHER INFORMATION: Xaa1= aza3K
<220> FEATURE:
<221> NAME/KEY: MISC_FEATURE
<222> LOCATION: (4)..(4)
<223> OTHER INFORMATION: Xaa2 = aza3(1)Nal
<220> FEATURE:
<221> NAME/KEY: MISC_FEATURE
<222> LOCATION: (5)..(5)
<223> OTHER INFORMATION: Xaa3= aza3L
<220> FEATURE:

-continued

```
<221> NAME/KEY: MISC_FEATURE
<222> LOCATION: (6)..(6)
<223> OTHER INFORMATION: Xaa4 = aza3(1)Nal

<400> SEQUENCE: 9

Leu Xaa Lys Xaa Xaa Xaa
1               5

<210> SEQ ID NO 10
<211> LENGTH: 6
<212> TYPE: PRT
<213> ORGANISM: Artificial Sequence
<220> FEATURE:
<223> OTHER INFORMATION: Cyclic peptide comprising three aza-B3-
      aminoacyle residues
<220> FEATURE:
<221> NAME/KEY: MISC_FEATURE
<222> LOCATION: (2)..(2)
<223> OTHER INFORMATION: Xaa1 = aza3K
<220> FEATURE:
<221> NAME/KEY: MISC_FEATURE
<222> LOCATION: (4)..(4)
<223> OTHER INFORMATION: Xaa2 = aza3(1)Nal
<220> FEATURE:
<221> NAME/KEY: MISC_FEATURE
<222> LOCATION: (6)..(6)
<223> OTHER INFORMATION: Xaa3 = aza3(1)Nal

<400> SEQUENCE: 10

Phe Xaa Lys Xaa Phe Xaa
1               5

<210> SEQ ID NO 11
<211> LENGTH: 5
<212> TYPE: PRT
<213> ORGANISM: Artificial Sequence
<220> FEATURE:
<223> OTHER INFORMATION: Cyclic peptide comprising three aza-B3-
      aminoacyle residues
<220> FEATURE:
<221> NAME/KEY: MISC_FEATURE
<222> LOCATION: (2)..(2)
<223> OTHER INFORMATION: Xaa1 = aza3K
<220> FEATURE:
<221> NAME/KEY: MISC_FEATURE
<222> LOCATION: (4)..(4)
<223> OTHER INFORMATION: Xaa2 = aza3L
<220> FEATURE:
<221> NAME/KEY: MISC_FEATURE
<222> LOCATION: (5)..(5)
<223> OTHER INFORMATION: Xaa3 = aza3(1)Nal

<400> SEQUENCE: 11

Leu Xaa Lys Xaa Xaa
1               5

<210> SEQ ID NO 12
<211> LENGTH: 5
<212> TYPE: PRT
<213> ORGANISM: Artificial Sequence
<220> FEATURE:
<223> OTHER INFORMATION: Cyclic peptide comprising three aza-B3-
      aminoacyle residues
<220> FEATURE:
<221> NAME/KEY: MISC_FEATURE
<222> LOCATION: (1)..(1)
<223> OTHER INFORMATION: Xaa1 = aza3K
<220> FEATURE:
<221> NAME/KEY: MISC_FEATURE
<222> LOCATION: (3)..(3)
<223> OTHER INFORMATION: Xaa2 = aza3(1)Nal
<220> FEATURE:
<221> NAME/KEY: MISC_FEATURE
<222> LOCATION: (5)..(5)
```

```
<223> OTHER INFORMATION: Xaa3 = aza3(1)Nal

<400> SEQUENCE: 12

Xaa Lys Xaa Leu Xaa
1               5

<210> SEQ ID NO 13
<211> LENGTH: 6
<212> TYPE: PRT
<213> ORGANISM: Artificial Sequence
<220> FEATURE:
<223> OTHER INFORMATION: Cyclic peptide comprising three aza-B3-
      aminoacyle residues
<220> FEATURE:
<221> NAME/KEY: MISC_FEATURE
<222> LOCATION: (2)..(2)
<223> OTHER INFORMATION: Xaa1=aza3K
<220> FEATURE:
<221> NAME/KEY: MISC_FEATURE
<222> LOCATION: (4)..(4)
<223> OTHER INFORMATION: Xaa2=aza3(1)Nal
<220> FEATURE:
<221> NAME/KEY: MISC_FEATURE
<222> LOCATION: (6)..(6)
<223> OTHER INFORMATION: Xaa3=aza3(4F-1)Nal

<400> SEQUENCE: 13

Leu Xaa Lys Xaa Leu Xaa
1               5

<210> SEQ ID NO 14
<211> LENGTH: 6
<212> TYPE: PRT
<213> ORGANISM: Artificial Sequence
<220> FEATURE:
<223> OTHER INFORMATION: Cyclic peptide comprising three aza-B3-
      aminoacyle residues
<220> FEATURE:
<221> NAME/KEY: MISC_FEATURE
<222> LOCATION: (2)..(2)
<223> OTHER INFORMATION: Xaa1 = aza3K
<220> FEATURE:
<221> NAME/KEY: MISC_FEATURE
<222> LOCATION: (4)..(4)
<223> OTHER INFORMATION: Xaa2 = aza3Oct
<220> FEATURE:
<221> NAME/KEY: MISC_FEATURE
<222> LOCATION: (6)..(6)
<223> OTHER INFORMATION: Xaa3 = aza3Oct

<400> SEQUENCE: 14

Lys Xaa Trp Xaa Trp Xaa
1               5

<210> SEQ ID NO 15
<211> LENGTH: 6
<212> TYPE: PRT
<213> ORGANISM: Artificial Sequence
<220> FEATURE:
<223> OTHER INFORMATION: Cyclic peptide containing three aza-B3-
      aminoacyle residues
<220> FEATURE:
<221> NAME/KEY: MISC_FEATURE
<222> LOCATION: (2)..(2)
<223> OTHER INFORMATION: Xaa1=aza3K
<220> FEATURE:
<221> NAME/KEY: MISC_FEATURE
<222> LOCATION: (3)..(3)
<223> OTHER INFORMATION: Xaa2=cha (cyclohexyalanine)
<220> FEATURE:
<221> NAME/KEY: MISC_FEATURE
<222> LOCATION: (4)..(4)
<223> OTHER INFORMATION: Xaa3=aza3Amy
<220> FEATURE:
```

```
<221> NAME/KEY: MISC_FEATURE
<222> LOCATION: (6)..(6)
<223> OTHER INFORMATION: Xaa4=aza3(1)Nal

<400> SEQUENCE: 15

Lys Xaa Xaa Xaa Trp Xaa
1               5

<210> SEQ ID NO 16
<211> LENGTH: 6
<212> TYPE: PRT
<213> ORGANISM: Artificial Sequence
<220> FEATURE:
<223> OTHER INFORMATION: Cyclic peptide comprising three aza-B3-
      aminoacyle residues
<220> FEATURE:
<221> NAME/KEY: MISC_FEATURE
<222> LOCATION: (2)..(2)
<223> OTHER INFORMATION: Xaa1 = aza3K
<220> FEATURE:
<221> NAME/KEY: MISC_FEATURE
<222> LOCATION: (3)..(3)
<223> OTHER INFORMATION: Xaa2 = Cha (cyclohexylalanine)
<220> FEATURE:
<221> NAME/KEY: MISC_FEATURE
<222> LOCATION: (4)..(4)
<223> OTHER INFORMATION: Xaa3 = aza3(4)Fpa
<220> FEATURE:
<221> NAME/KEY: MISC_FEATURE
<222> LOCATION: (6)..(6)
<223> OTHER INFORMATION: Xaa4 = aza3Cha

<400> SEQUENCE: 16

Arg Xaa Xaa Xaa Trp Xaa
1               5

<210> SEQ ID NO 17
<211> LENGTH: 6
<212> TYPE: PRT
<213> ORGANISM: Artificial Sequence
<220> FEATURE:
<223> OTHER INFORMATION: Cyclic peptide comprising three aza-B3-
      aminoacyle residues
<220> FEATURE:
<221> NAME/KEY: MISC_FEATURE
<222> LOCATION: (2)..(2)
<223> OTHER INFORMATION: Xaa1 = aza3K
<220> FEATURE:
<221> NAME/KEY: MISC_FEATURE
<222> LOCATION: (4)..(4)
<223> OTHER INFORMATION: Xaa2 = aza3(2)Nal
<220> FEATURE:
<221> NAME/KEY: MISC_FEATURE
<222> LOCATION: (6)..(6)
<223> OTHER INFORMATION: Xaa3 = aza3(2)Nal

<400> SEQUENCE: 17

Leu Xaa Lys Xaa Leu Xaa
1               5

<210> SEQ ID NO 18
<211> LENGTH: 6
<212> TYPE: PRT
<213> ORGANISM: Artificial Sequence
<220> FEATURE:
<223> OTHER INFORMATION: Cyclic peptide comprising three aza-B3-
      aminoacyle residues
<220> FEATURE:
<221> NAME/KEY: MISC_FEATURE
<222> LOCATION: (2)..(2)
<223> OTHER INFORMATION: Xaa1 = aza3K
<220> FEATURE:
<221> NAME/KEY: MISC_FEATURE
<222> LOCATION: (4)..(4)
```

```
<223> OTHER INFORMATION: Xaa2 = aza3(2)Nal
<220> FEATURE:
<221> NAME/KEY: MISC_FEATURE
<222> LOCATION: (6)..(6)
<223> OTHER INFORMATION: Xaa3 = aza3(2)Nal

<400> SEQUENCE: 18

Phe Xaa Arg Xaa Phe Xaa
1               5

<210> SEQ ID NO 19
<211> LENGTH: 6
<212> TYPE: PRT
<213> ORGANISM: Artificial Sequence
<220> FEATURE:
<223> OTHER INFORMATION: Cyclic peptide comprising three aza-B3-
      aminoacyle residues
<220> FEATURE:
<221> NAME/KEY: MISC_FEATURE
<222> LOCATION: (2)..(2)
<223> OTHER INFORMATION: Xaa1 = aza3K
<220> FEATURE:
<221> NAME/KEY: MISC_FEATURE
<222> LOCATION: (4)..(4)
<223> OTHER INFORMATION: Xaa2 = aza3(1)Nal
<220> FEATURE:
<221> NAME/KEY: MISC_FEATURE
<222> LOCATION: (6)..(6)
<223> OTHER INFORMATION: Xaa3 = aza3(4)Fluo-(1)Nal

<400> SEQUENCE: 19

Leu Xaa Lys Xaa Leu Xaa
1               5

<210> SEQ ID NO 20
<211> LENGTH: 6
<212> TYPE: PRT
<213> ORGANISM: Artificial Sequence
<220> FEATURE:
<223> OTHER INFORMATION: Cyclic peptide comprising three aza-B3-
      aminoacyle residues
<220> FEATURE:
<221> NAME/KEY: MISC_FEATURE
<222> LOCATION: (2)..(2)
<223> OTHER INFORMATION: Xaa1 = aza3K
<220> FEATURE:
<221> NAME/KEY: MISC_FEATURE
<222> LOCATION: (4)..(4)
<223> OTHER INFORMATION: Xaa2 = aza3Bip
<220> FEATURE:
<221> NAME/KEY: MISC_FEATURE
<222> LOCATION: (6)..(6)
<223> OTHER INFORMATION: Xaa3 = aza3Bip

<400> SEQUENCE: 20

Leu Xaa Lys Xaa Leu Xaa
1               5

<210> SEQ ID NO 21
<211> LENGTH: 5
<212> TYPE: PRT
<213> ORGANISM: Artificial Sequence
<220> FEATURE:
<223> OTHER INFORMATION: Cyclic peptide comprising three aza-B3-
      aminoacyle residues
<220> FEATURE:
<221> NAME/KEY: MISC_FEATURE
<222> LOCATION: (1)..(1)
<223> OTHER INFORMATION: Xaa1 = aza3K
<220> FEATURE:
<221> NAME/KEY: MISC_FEATURE
<222> LOCATION: (3)..(3)
<223> OTHER INFORMATION: Xaa2 = aza3Bip
<220> FEATURE:
```

```
<221> NAME/KEY: MISC_FEATURE
<222> LOCATION: (5)..(5)
<223> OTHER INFORMATION: Xaa3 = aza3Bip

<400> SEQUENCE: 21

Xaa Lys Xaa Leu Xaa
1               5

<210> SEQ ID NO 22
<211> LENGTH: 5
<212> TYPE: PRT
<213> ORGANISM: Artificial Sequence
<220> FEATURE:
<223> OTHER INFORMATION: Cyclic peptide comprising three aza-B3-
      aminoacyle residues
<220> FEATURE:
<221> NAME/KEY: MISC_FEATURE
<222> LOCATION: (2)..(2)
<223> OTHER INFORMATION: Xaa1 = aza3R
<220> FEATURE:
<221> NAME/KEY: MISC_FEATURE
<222> LOCATION: (4)..(4)
<223> OTHER INFORMATION: Xaa2 = aza3(1)Nal

<400> SEQUENCE: 22

Leu Xaa Arg Xaa Leu
1               5

<210> SEQ ID NO 23
<211> LENGTH: 5
<212> TYPE: PRT
<213> ORGANISM: Artificial Sequence
<220> FEATURE:
<223> OTHER INFORMATION: Cyclic peptide comprising two aza-B3-
      aminoacyle residues
<220> FEATURE:
<221> NAME/KEY: MISC_FEATURE
<222> LOCATION: (2)..(2)
<223> OTHER INFORMATION: Xaa1 = aza3K
<220> FEATURE:
<221> NAME/KEY: MISC_FEATURE
<222> LOCATION: (5)..(5)
<223> OTHER INFORMATION: Xaa2 = aza3(1)Nal

<400> SEQUENCE: 23

Leu Xaa Lys Leu Xaa
1               5

<210> SEQ ID NO 24
<211> LENGTH: 5
<212> TYPE: PRT
<213> ORGANISM: Artificial Sequence
<220> FEATURE:
<223> OTHER INFORMATION: Cyclic peptide comprising three aza-B3-
      aminoacyle residues
<220> FEATURE:
<221> NAME/KEY: MISC_FEATURE
<222> LOCATION: (1)..(1)
<223> OTHER INFORMATION: Xaa1 = aza3K
<220> FEATURE:
<221> NAME/KEY: MISC_FEATURE
<222> LOCATION: (3)..(3)
<223> OTHER INFORMATION: Xaa2 = aza3(2)Nal
<220> FEATURE:
<221> NAME/KEY: MISC_FEATURE
<222> LOCATION: (5)..(5)
<223> OTHER INFORMATION: Xaa3 = aza3(2)Nal

<400> SEQUENCE: 24

Xaa Arg Xaa Phe Xaa
1               5
```

```
<210> SEQ ID NO 25
<211> LENGTH: 5
<212> TYPE: PRT
<213> ORGANISM: Artificial Sequence
<220> FEATURE:
<223> OTHER INFORMATION: Cyclic peptide comprising three aza-B3-
      aminoacyle residues
<220> FEATURE:
<221> NAME/KEY: MISC_FEATURE
<222> LOCATION: (1)..(1)
<223> OTHER INFORMATION: Xaa1 = aza3K
<220> FEATURE:
<221> NAME/KEY: MISC_FEATURE
<222> LOCATION: (3)..(3)
<223> OTHER INFORMATION: Xaa2 = aza3(2)Nal
<220> FEATURE:
<221> NAME/KEY: MISC_FEATURE
<222> LOCATION: (5)..(5)
<223> OTHER INFORMATION: Xaa3 = aza3(2)Nal

<400> SEQUENCE: 25

Xaa Lys Xaa Leu Xaa
1               5
```

CYCLIC PEPTIDES COMPRISING AT LEAST ONE AZA-β3-AMINOACYL RESIDUE AND THEIR USES

A subject of the present invention is cyclic peptides comprising at least one azaβ³ aminoacyl residue, as well as their uses in pharmaceutical compositions.

Most of the available anti-infective medicaments belong to the class of small chemical molecules but numerous projects in the research and development stage are currently concerned with the class of therapeutic peptides.

In fact the anti-infective properties of certain peptides are the subject of useful discoveries in the antibacterial field, as bacterial strains are becoming more and more resistant to antimicrobial agents, hence the need to find novel active molecules.

Recently, one group has shown that it could construct very small antibacterial and antifungal peptides constituted by only four amino acids. One of the amino acids is replaced by its enantiomer and a chain of fatty acids is attached to the peptide sequence ($C_{16}$-KKkK). In this case, the three-dimensional structure does not seem critical for the anti-infective activity of the peptide (Makovitzki A., Avrahami D., Shai, Y. PNAS, 2006, 10, 15997). On the other hand, the peptide sequence and the length of the fatty acid determine the spectrum of antimicrobial activity.

A new family has also been described, i.e. cyclic peptides, alternating L and D amino acids (Fernandez-Lopez S., Kim H S., Choi E., Delgado M. Granja J R., Khazanov A., Kraehenbuehl K., Long G., Weinberger D A, Wilcoxen K M., Ghadiri M R., Nature., 2001, 412, 452; Dartois, V., Sanchez-Quesada J., Cabezas E., Chi E., Dubbelde C., Dunn C., Granja J., Gritzen C., Weinbeiger D., Ghadiri M. R., Parr T. R. Antimicrob. Agents Chemother. 2005, 49, 3302; WO 02/090503). These synthetic peptides having antimicrobial properties are self-structuring and are able to target the microbial membranes, then to form gaps therein, leading to the destruction of the bacteria in vitro and in-vivo.

This diversity of structures and types of action confers upon the antimicrobial peptides a very strong anti-infective agent potential in the face of multi-resistant bacteria. Several molecules are moreover in an advanced stage of development in the context of localized infections and the first candidates against systemic infections are currently undergoing evaluation.

These antimicrobial peptides are one of the key elements of the innate immune defence of multicellular organisms and are thus present in both the animal and plant kingdoms. Also, peptide-based nanostructures offer numerous possible variations and make it possible to access new nanoscopic subjects.

In order to confront the emergence of new pathogens and especially the appearance of multi-resistant microorganisms, it is essential to identify new antibiotics.

However, the use of the peptides is limited by rapid elimination in a biological medium and metabolic instability linked to their rapid degradation by the peptidases at the level of the amide bonds. Moreover with the exception of the purely biological structures, there are few biomimetic antimicrobial pseudopeptides having greater activity and stability than the native peptide.

The Inventors have also developed the synthesis of amino acid analogues, the aza-β³-amino acids, which, once incorporated into the peptide sequences, form pseudopeptides with an improved lifetime.

These aza-β³-amino acids or N"-substituted hydrazino acetic acids (Cheguillaume A., Doubli-Bounoua I., Baudy-Floc'h M., Le Grel P. Synlett, 2000, 3, 331; WO 2004/111086) are monomers which can be considered as aza derivatives of the β³-amino acids. The aza-β³-amino acids bear their side chain on a nitrogen atom of non-fixed configuration, a modification which is reflected in a loss of chirality of the monomer compared with the β³-amino acids. However due to the more or less rapid nitrogen inversion, this monomer will be able to mimic the orientation of the side chain of a β³-amino acid of R or S configuration. On the other hand, the extension of the chain by a methylene group will contribute a certain flexibility to the monomer.

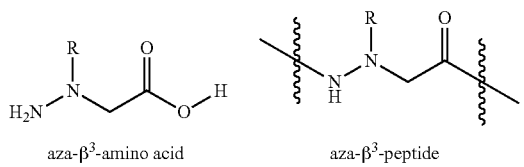

aza-β³-amino acid       aza-β³-peptide

The aza-β³-peptides which are aza analogues of the β³-peptides.

The capacity for inversion of the side chain configuration at the level of the nitrogen atom was validated by the crystallization of cyclic aza-β³-hexapeptides. In fact, X-ray study of these crystals shows that the nitrogen atoms bearing the side chains of these oligomers alternate R and S configuration along the entire sequence. The aza-β³-cyclohexapeptides therefore exist in the form of two invertomers in equilibrium similar to the two chair forms of the cyclohexane (Le Grel P., Salatün A., Potel M., Le Grel B., Lassagne F., J. Org. Chem. 2006)

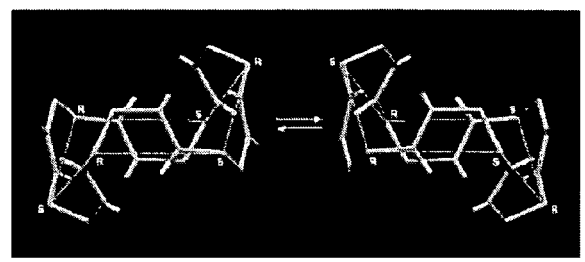

Three-dimensional representation of an aza-β³-cyclohexapeptide in the crystalline state.

The aza-β³-amino acids can therefore adopt both configurations and are able to form hydrogen bonds.

Unexpectedly, the Inventors discovered that by alternating fixed-configuration α-amino acids and aza-β³-amino acids in cyclic peptides, the configuration of the nitrogen atoms is fixed, thus forming chiral structures having side chains which are appropriate in order to form nanotubes capable of perforating the membranes of the bacteria.

A further subject of the present invention is cyclic peptides having a random alternation of L-α-aminoacyl residues and aza-β³-aminoacyl residues corresponding to formula (A) below:

(A)

in which

R1 represents a side chain chosen from the group comprising proteogenic and non-proteogenic chains, providing that two L-α-aminoacyl residues are separated by at least one aza-β³-aminoacyl residue and that the total number of the L-α-aminoacyl residues and the aza-β³-aminoacyl residues is comprised between 4 and 8.

By proteogenic is meant, within the meaning of the present invention, all the natural or synthetic amino acids constituting proteins or polypeptides, in particular: aspartic acid (Asp or D), asparagine (Asn or N), threonine (Thr or T), serine (Ser or S), glutamic acid (Glu or E), glutamine (Gln or Q), glycine (Gly or G), alanine (Ala or A), cysteine (Cys or C), valine (Val or V), methionine (Met or M), isoleucine (Ile or I), leucine (Leu or L), tyrosine (Tyr or Y), phenylalanine (Phe or F), histidine (His or H), lysine (Lys or K), tryptophan (Trp or W), proline (Pro or P) and arginine (Arg or R).

In an advantageous embodiment of the invention, the cyclic peptides are chosen from the tetrapeptides, pentapeptides, hexapeptides, heptapeptides and octapeptides, the hexapeptides and octapeptides being particularly advantageous.

Advantageously, the L-α-aminoacyl residues are chosen from the group comprising the residues of the following amino acids: arginine (Arg or R), leucine (Leu or L), lysine (Lys or K), phenylalanine (Phe or F), serine (Ser or S), threonine (Thr or T) and tryptophan (Tryp or W) and from the aza-β³-aminoacyl residues of formula (A), R1 is chosen from the group comprising natural amino acid residues or non-natural amino acid residues.

In a further advantageous embodiment of the invention the natural amino acid residues entering into the structure of the aza-β³-aminoacyl residues are chosen from the group comprising arginine, leucine, lysine, phenylalanine, serine, threonine and tryptophan residues and the non-natural amino acids residues are chosen from the group comprising 1-naphthylalanine [(1)Nal], 2-naphthylalanine [(2)Nal], 4-phenyl-phenylalanine (4Bip), diphenylalanine (Dip), 9-anthracenylalanine [(9)Ath], 4-pyridylalanine [(4)Pal], 3-pyridylalanine [(3)Pal], 2-pyridylalanine [(2)Pal], fluorophenylalanine (4-Fpa), dodecylalanine (Amy), nonylalanine (Non), octylalanine (Oct), cyclohexylalanine (Cha), 4-fluoro-1-naphthylalanine (4-F-1-Nal), homoserine (Hse), and homo γ-hydroxythreonine and norleucine (Nle) residues.

In a particularly advantageous embodiment of the invention, the cyclic peptides have the sequence (Ia):

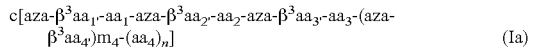

in which, each of $aa_1$, $aa_2$, $aa_3$, and $aa_4$ represents independently of each other an L-α-aminoacyl residue, each of aza-β³$aa_{1'}$, aza-β³$aa_{2'}$, aza-β³$aa_{3'}$ and aza-β³$aa_{4'}$ represents independently of each other an aza-β³-amino acid, corresponding to formula (A), and $m_4$ and $n_4$ each simultaneously represent 0 or 1, or the sequence (Ib):

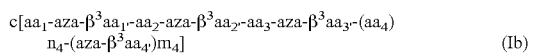

in which, each of $aa_1$, $aa_2$, $aa_3$, and $aa_4$ represents independently of each other an L-α-aminoacyl residue, each of aza-β³$aa_{1'}$, aza-β³$aa_{2'}$, aza-β³$aa_{3'}$, and aza-β³$aa_4$ represents independently of each other an aza-β³-amino acid, corresponding to formula (A), and $m_4$ and $n_4$ each simultaneously represent 0 or 1.

or the sequence (Ic):

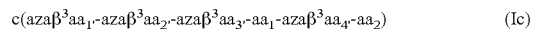

in which, each of $aa_1$ and $aa_2$ represents independently of each other an L-α-aminoacyl residue, each of aza-β³$aa_1$, aza-β³$aa_{2'}$, aza-β³$aa_3$, and aza-β³$aa_4$ represents independently of each other an aza-β³-amino acid, corresponding to formula (A) or the sequence (Id):

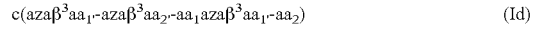

in which, each of $aa_1$ and $aa_2$ represents independently of each other an L-α-aminoacyl residue, each of aza-β³$aa_{1'}$, and aza-β³$aa_2$ represents independently of each other an aza-β³-amino acid, corresponding to formula (A).

In a particular embodiment of the invention, the cyclic peptides are chosen from the group comprising the following sequences:

SEQ ID NO 1: c[-Leu-*aza*β³Lys-Lys-*aza*β³(1)Nal-Leu-*aza*β³(1)Nal-](NafNaf),

SEQ ID NO 2: c[-Lys-*aza*β³Lys-Leu-*aza*β³(1)Nal-Leu-*aza*β³(1)Nal-](NalNal),

SEQ ID NO 3: c[-Lys-*aza*β³Lys-Trp-*aza*β³Leu-Trp-*aza*β³Leu-](TrypTryp),

SEQ ID NO 4: c[-Lys-*aza*β³Lys-Lys-*aza*β³Leu-Trp-*aza*β³Leu-](3KW),

SEQ ID NO 5: c[-Trp-*aza*β³Lys-Lys-*aza*β³Lys-Trp-*aza*β³Leu-](3K2),

SEQ ID NO 6: c[-Lys-*aza*β³Lys-Lys-*aza*β³Lys-Trp-*aza*β³(1)Nal-](4KW),

SEQ ID NO 7: c[-Ser-*aza*β³(1)Nal-Phe-*aza*β³Lys-Thr-*aza*β³Lys-Ser-*aza*β³Lys-](SNalF), SEQ ID NO 8: c[Leu-*aza*β³Arg-Arg-*aza*β³(1)Nal-Leu-*aza*β³(1)Nal-](RNaf), SEQ ID NO 9: c[-Leu-*aza*β³Lys-Lys-*aza*β³(1)Nal-]*aza*β³Leu-*aza*β³(1)Nal-](Nafaza)

SEQ ID NO 10: c[-Phe-*aza*β³Lys-Lys-*aza*β³(1)Nal-Phe-*aza*β³(1)Nal-](PheNal),

SEQ ID NO 11: c[-Leu-*aza*β³Lys-Lys-*aza*β³Leu-*aza*β³(1)Nal-](5pNala),

SEQ ID NO 12: c[-*aza*β³Lys-Lys-*aza*β³(1)Nal-Leu-*aza*β³(1)Nal-](5pNafa).

SEQ ID NO 13: c[-Leu-*aza*β³Lys-Lys-*aza*β³(1)-Nal-Leu-*aza*β³(4F-1)Nal-](4Fluo1Naf), SEQ ID NO 14: c[-Lys-*aza*β³Lys-Trp-*aza*β³Oct-Trp-*aza*β³Oct-](OctOct), -continued SEQ ID NO 15: c[-Lys-*aza*β³Lys-Cha-*aza*β³Amy-Trp-*aza*β³(1)Nal-](Chado), SEQ ID NO 16: c[-Arg-*aza*β³Lys-Cha-*aza*β³(4)Fpa-Trp-*aza*β³Cha-](FluoKil), SEQ ID NO 17: c[-Leu-*aza*β³Lys-Lys-*aza*β³(2)Nal-Leu-*aza*β³(2)Nal-](Naf2Naf2), SEQ ID NO 18: c[-Phe-*aza*β³Lys-Arg-*aza*β³(2)Nal-Phe-*aza*β³(2)Nal-](PheNar2), SEQ ID NO 19: c[-Leu-*aza*β³Lys-Lys-*aza*β³(1)Nal-Leu-*aza*β³(4)Fluo-(1)Nal-](4FluoNaf), SEQ ID NO 20: c[-Leu-*aza*β³Lys-Lys-*aza*β³Bip-Leu-*aza*β³Bip-](BipBip), SEQ ID NO 21: c[-*aza*β³Lys-Lys-*aza*β³Bip-Leu-*aza*β³Bip-](5pBip), SEQ ID NO 22: c[-Leu-*aza*β³Arg-Arg-*aza*β³(1)Nal-Leu-](5pRNaf), SEQ ID NO 23: c[-Leu-*aza*β³Lys-Lys-Leu-*aza*β³(1)Nal-](5pNafaza), SEQ ID NO 24: c[-*aza*β³Lys-Arg-*aza*β³(2)Nal-Phe-*aza*β³(2)Nal-](5pPheNar2), SEQ ID NO 25: c[-*aza*β³Lys-Lys-*aza*β³(2)Nal-Leu-*aza*β³(2)Nal-](5pNaf2), The cyclic peptides according to the invention have the advantage of totally excluding the presence of D-α-amino acids, which are non-natural amino acids having a high cost.

According to the invention, the cyclic peptides can be prepared by any technique known to a person skilled in the art from products available on the market or prepared according to techniques described in the literature. They can in particular be prepared according to the technique described by Busnel O, Bi L, Dali H, Cheguillaume A, Chevance S, Bondon A, Muller S, Baudy-Floc'h M., J Org. Chem. 2005 Dec. 23; 70(26):10701-8.

The cyclic peptides according to the invention were found to be active on bacterial strains, in particular on Gram-negative bacteria of Group 2 (pathogens): *Escherichia coli, Salmonella thyphimurium, Pseudomonas aeruginosa, Klebsiella pneumoniae* and Gram-positive bacteria: *Bacillus megaterium* (group 1) and *Streptococcus aureus* (group 2).

On the other hand, these cyclic pseudopeptides do not cause blood cell lysis and are only slightly or not at all cytotoxic at concentrations in which they nevertheless inhibit bacterial proliferation of pathogenic bacteria.

The cyclic peptides according to the invention can be used as medicaments or for disinfection and antisepsis (surface disinfection, etc.) for humans or animals, in particular for mammals and birds.

Advantageously they can be used as anti-infective or antimicrobial agents, in particular as anti-bacterials, antibiotics, anti-parasitics, antivirals, anti-mycotics or anti-fungals.

A subject of the invention is also pharmaceutical compositions comprising at least one cyclic peptide according to the invention.

In this context they can be used in combination with any pharmaceutically acceptable excipient and in any pharmaceutically acceptable form such as for example tablets, gelatin capsules, capsules, soaps and lotions.

In an advantageous embodiment of the invention, the cyclic peptides can be combined with at least one other anti-infective agent, in particular chosen from the group comprising penicillin, vancomycin, erythromycin, or with other therapeutic agents.

According to the invention, the cyclic peptides can therefore be used for treating all the infectious diseases, in particular nosocomial infections, tuberculosis, septicaemia, pneumonia and respiratory diseases.

A subject of the invention is therefore also the use of the cyclic peptides according to the invention for preparing a medicament intended for the treatment of the infectious diseases chosen from the group comprising in particular nosocomial infections, tuberculosis, septicaemia, pneumonia and respiratory diseases.

A further purpose of the invention is a method for the treatment of infections in humans or animals in which microbial cells are brought into contact with at least one cyclic peptide according to the invention in a quantity sufficient to cause the death of the microbial cells without causing the death of the cells of said human or said animal. They can also be used as disinfectants in cosmetology, for the disinfection of surfaces or in the agri-food sector.

Examples 1 and 2 and FIGS. 1 to 6 below illustrate the invention.

FIG. 1 shows the synthesis of the NafNaf peptide according to Example 1.

FIG. 2A represents the minimum inhibitory concentrations (MIC) of bacterial proliferation of peptides according to the invention on different strains; the first value corresponds to the lowest concentration inhibiting the bacterial activity and the second value corresponds to the last concentration at which bacterial growth is still observed, the MIC value being comprised between these two values; FIG. 2B represents the minimum bactericidal concentrations (MBC) of the NafNaf peptide on different strains.

FIG. 3 represents the antibacterial activity of the NafNaf peptide at increasing doses on *Staphylococcus aureus* measured according to Example 2. The column "PBB+Bact" corresponds to the control where the bacteria are not exposed to the presence of pseudopeptides, the column "PBB" corresponds to the control without bacteria and the column "Ampi 1 µg/ml" corresponds to the ampicillin used as an antibacterial activity control.

FIG. 4 represents the antibacterial activity of the NafNaf peptide at increasing doses on *Salmonella typhimurium* measured according to Example 2. The column "PBB+Bact" corresponds to the control where the bacteria are not exposed to the presence of pseudopeptides, the column "PBB" corresponds to the control without bacteria and the column "Ampi 1 µg/ml" corresponds to the ampicillin used as control of an antibacterial activity.

FIG. 7 represents the minimum inhibitory concentrations (MIC) of bacterial proliferation after 48 hours in the rich culture medium TSB (Tryptic Soy Broth) on different strains for peptides according to the invention. The antibacterial activity is measured according to Example 5. ND: Antibacterial activity not detected within the range of concentrations tested; +Gram-positive bacteria; −Gram-negative bacteria.

Figure 8:
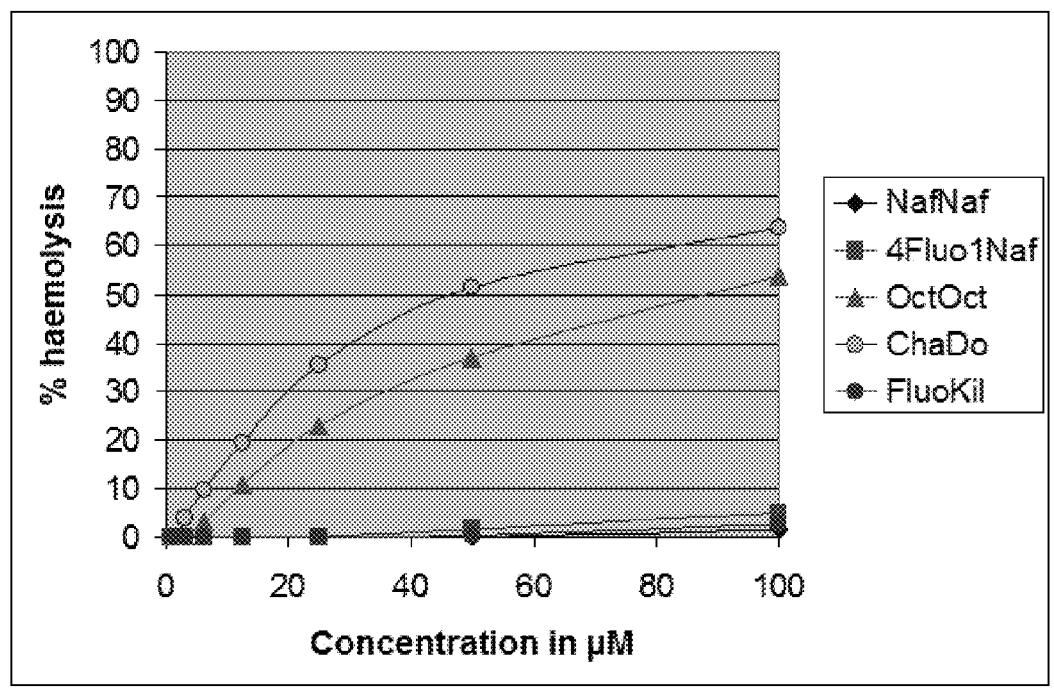

FIG. 8 shows the haemolytic activity curve of peptides according to the invention measured according to the method described in Example 6.

EXAMPLE 1

Preparation of the NafNaf Cyclic Pseudopeptide

Figure 1:
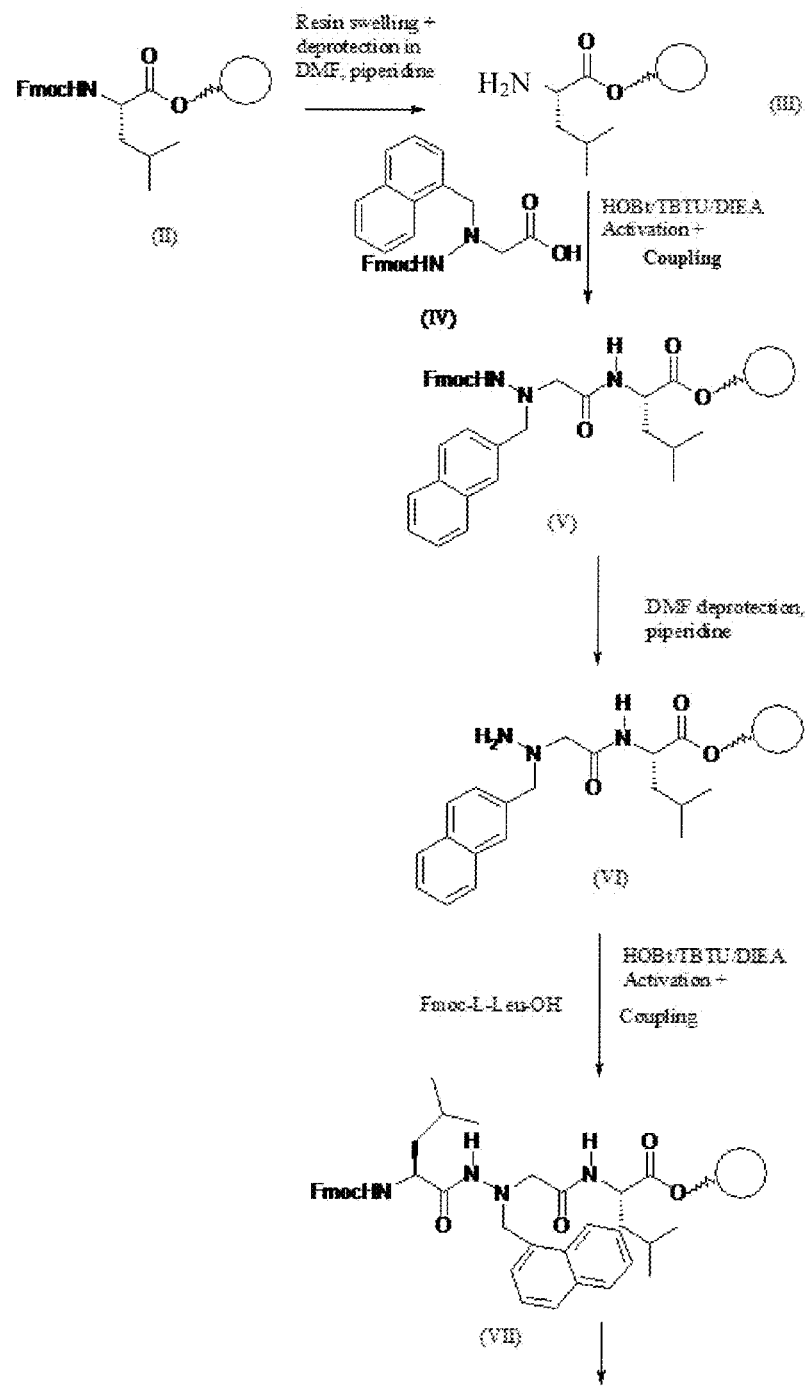
Figure 1:
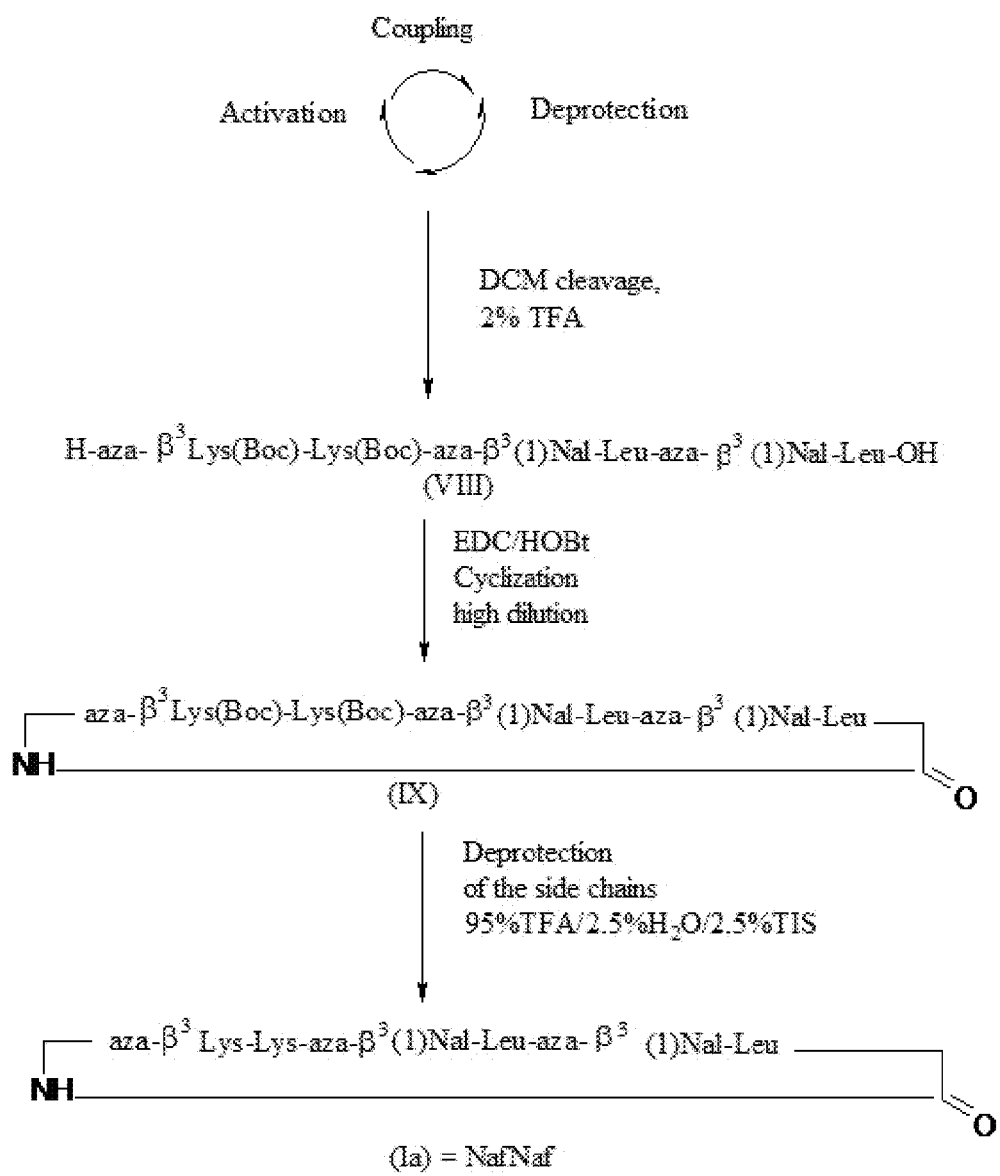

This is given in FIG. 1. The roman numerals used in the paragraph below refer to said figure.

A resin based on 2-chlorotrityl chloride loaded at a rate of 1 mmol/g, with L-leucine, the amine function of which is protected by an Fmoc (9-Fluorenylmethyloxycarbonyl) group (II) is placed in a continuous flow of dimethylformamide (DMF) to swell for 5 minutes. The amine group of the leucine fixed to the resin is deprotected by passing over the resin a 20% piperidine solution in DMF in order to produce (III); the Fmoc-aza-$\beta^3$-(1)Nal-OH of formula (IV) is activated by a mixture of N-Hydroxybenzotriazole/O-benzotriazole-N,N,N',N'-tetramethyl-uronium-hexafluorophosphate/N-Ethyldiisopropyl amine (HOBt/TBTU/DIEA) in the proportions (1/1/2) in solution in DMF then coupled to the deprotected resin (III) over 2 hours in a continuous flow to produce (V). Deprotection of the amine group is then carried out by elimination of the Fmoc group by passing over the resin a 20% piperidine solution in DMF in order to produce (VI) then coupling is again carried out under the conditions described previously in order to obtain (VII). The activation-coupling—deprotection cycle is repeated as many times as required, then the final peptide is separated from its support by cleavage in dichloromethane (DCM) containing 2% trifluoroacetic acid (TFA). The compound of formula (VIII) is obtained, which is cyclized in a 1-ethyl-3-(3-dimethylaminopropyl)carbodiimide (EDC)/HOBt medium at high dilution ($4.10^{-4}$ M) in the presence of 4 equivalents of coupling agents HOBt, EDC and DIEA; this cyclization takes two days. Compound (IX) is obtained and treated with a TFA/$H_2O$/TIS (95/2.5/2.5) mixture in order to deprotect the side chains and obtain compound (Ia) or NafNaf.

EXAMPLE 2

Measurement of the Antibacterial Activity in a PB Poor Medium 2.1. Method of Operation The tests were carried out on Gram-negative bacterial strains of Group 2 (pathogens): *Escherichia coli, Salmonella thyphimurium, Pseudomonas aeruginosa, Klebsiella pneumonie* and on Gram-positive strains: *Bacillus megaterium* (group 1) and *Streptococcus aureus* (group 2).

The bacteria are incubated in a PB poor medium in the case of the bacteria: *Escherichia coli, Pseudomonas aeruginosa, Klebsiella pneumoniae, Bacillus megaterium* and in a poor medium enriched with beef extract PBB in the case of two other bacteria: *Streptococcus aureus* and *Salmonella thyphimurium* with increasing concentrations of peptides or analogues ranging from 1 to 320 µg/ml. This test is carried out in 96-well microplates. After incubation for 18 hours at 30° C. or 37° C., the optical density of the microplates is read at 595 nm in order to evaluate the bacterial growth and determine the minimum inhibitory concentration (MIC) for each molecule tested. Each measurement is performed in triplicate.

Moreover, the minimum bactericidal concentration (MBC) is determined by plating the contents of the wells where there is an absence of bacterial growth on dishes containing rich media (Luria broth or (LB) or Brain Heart Infusion (BHi). The MBC corresponds to the concentration at which no bacterial colony is detected after incubation for 24 hours at 30 or 37° C.

2.2. Results

Figure 3:
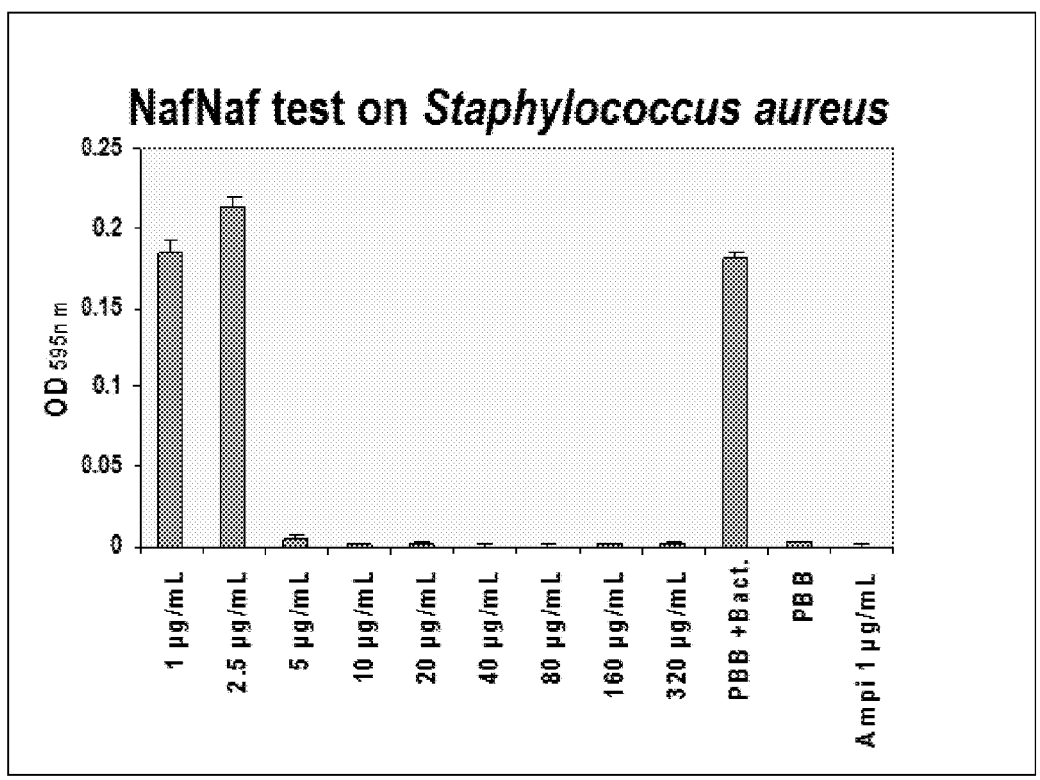
Figure 4:
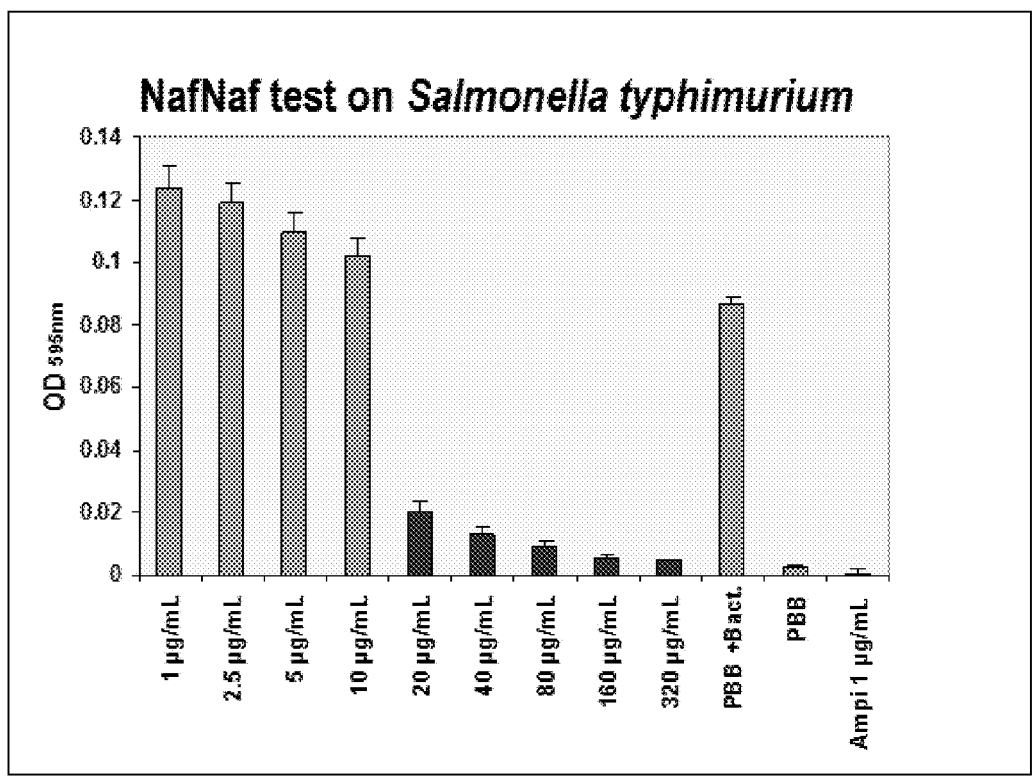

These are given in the table in FIG. 2 and in FIGS. 3 and 4.

The five sequences tested are found to be active although only two sequences (NafNaf and TrypTryp) have minimum inhibitory concentrations (MICs) of bacterial proliferation of less than 100 µg/mL (FIG. 2).

The NafNaf sequence has MICs of less than 100 µg/mL against all the bacteria tested (FIG. 2).

This peptide is very active on the golden *staphylococcus* (*Streptococcus aureus*) responsible for numerous nosocomial diseases with an MIC of less than 5 µg/mL and an MBC of less than 10 µg/mL (FIG. 2).

It is also active on the relatively resistant Gram-negative pathogenic bacteria such as *K. pneumoniae* responsible for respiratory and intestinal infections (FIG. 2). Its antimicrobial activity is comparable to that of the best cyclic peptides alternating D and L amino acids with MICs of approximately ten µg/mL in the case of the Gram-positive bacteria and comprised between 15 and 80 µg/mL in the case of the Gram-negative.

The NafNaf pseudopeptide is active at useful concentrations on all of the strains studied, in particular on pathogenic bacteria such as *Streptococcus aureus* and *Salmonella thyphimurium* where it is active at concentrations of less than 20 µg/mL. (FIGS. 3 and 4).

The Ampicillin (Ampi) chosen as reference is active from 1 µg/ml in the case of *Streptococcus aureus* and *Salmonella thyphimurium*. This concentration can be variable depending on the bacterial strain studied.

EXAMPLE 3

Measurement of the Haemolytic Activity of the NafNaf Peptide on Rabbit Erythrocytes 3.1. Operating Procedure The haemolytic activity of the pseudopeptides is tested on rabbit blood cells. Fresh rabbit erythrocytes are washed three times with a phosphate buffer saline [PBS buffer (pH 7.4)] by centrifugation for 5 min at 900 g and the final pellet is suspended in PBS. The NafNaf pseudopeptide solutions diluted in PBS (90 µL) are arranged in a 96-well plate. 90 µL of 2% rabbit erythrocyte solution (v/v) is added to these solutions to give a final volume of 180 µL and a concentration of 1% (v/v) blood cells. The suspensions obtained are incubated for 1 hour at 37° C. The samples are then centrifuged at 500 g for 5 min. 100 µL of supernatant of each sample is transferred into a new 96-well plate. The release of the haemoglobin is quantified by measuring the absorbance at 415 nm of the supernatant using a microplate reader. The controls corresponding to the absence of haemolysis (white) and to a 100% haemolysis consist, respectively, of the addition of 90 µL of PBS buffer and 90 µL of a 2% solution of Triton X-100 to the 90 µL of 2% blood cell solution. Each measurement is carried out in triplicate.

3.2. Results

Figure 5:
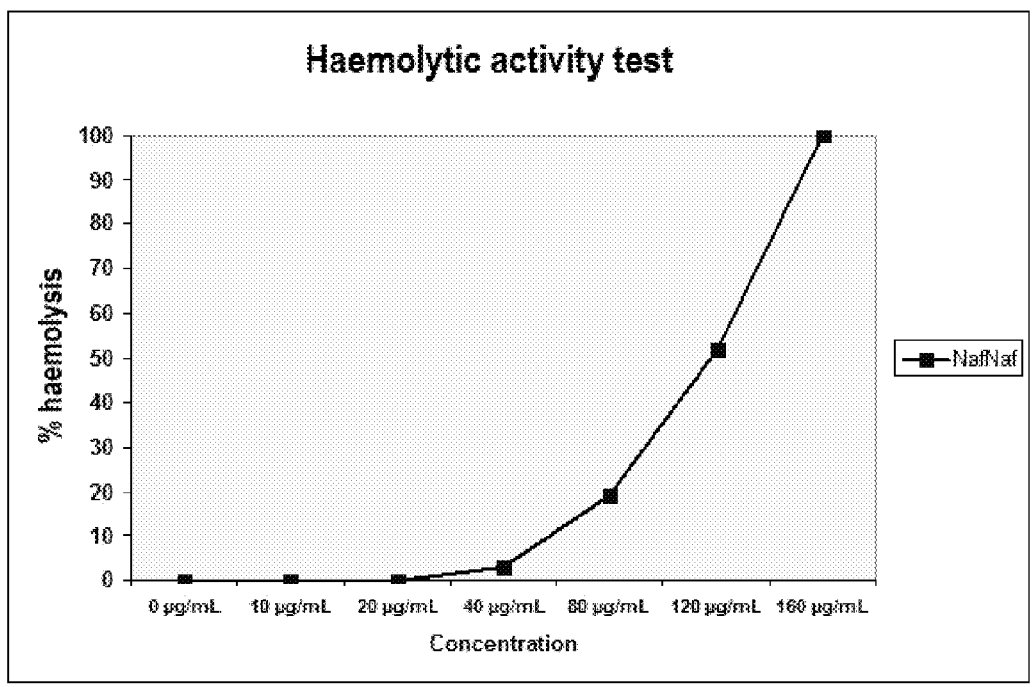
FIG. 5 represents the haemolytic activity curve of the NafNaf cyclic pseudopeptide measured according to the method described in Example 3.

These are given in FIG. 5.

The concentration of the NafNaf peptide at which 50% haemolysis takes place is 120 µg/mL.

This concentration is higher than that of the cyclic peptide of similar structure alternating the L and D amino acids and represented by the formula below:

[-(D)Lys-(L)Lys-(D)Leu-(L)Trp-(D)Leu-(L)Trp-]

which is haemolytic at 80 µg/mL.

Thus NafNAf exhibits no haemolytic activity at the concentrations at which it is bactericidal, in particular it has no action on the erythrocytes at 20 µg/mL, a concentration at which it is bactericidal for *Staphylococcus aureus* and *Salmonella typhimurium*.

EXAMPLE 4

In Vitro Evaluation of Cytotoxicity 4.1. Operating Procedure

The effects of the different cyclic pseudopeptides on cell growth are evaluated in sterile 96-well plates. The cells are seeded at $5.10^5$ cells per mL of culture medium (100 µL per well). The different pseudopeptides (10 µL per well) diluted in a saline solution are added at the time of seeding at the appropriate concentration (from 1 µg/mL to 1 mg/mL). The incubations are carried out at 37° C. under a humidified atmosphere containing 5% $CO_2$ for 24 or 48 hours.

After exposure to the compounds, the cell growth is assessed by measuring the formation of formazan from 3-(4, 5-dimethylthiazol-2-yl)-2,5-diphenyltetrazolium (MTT). The absorbance at 540 nm is measured by a Titertek Multiscan MCC/340 microplate reader. Each measurement is carried out in triplicate.

4.2. Results

Figure 6:
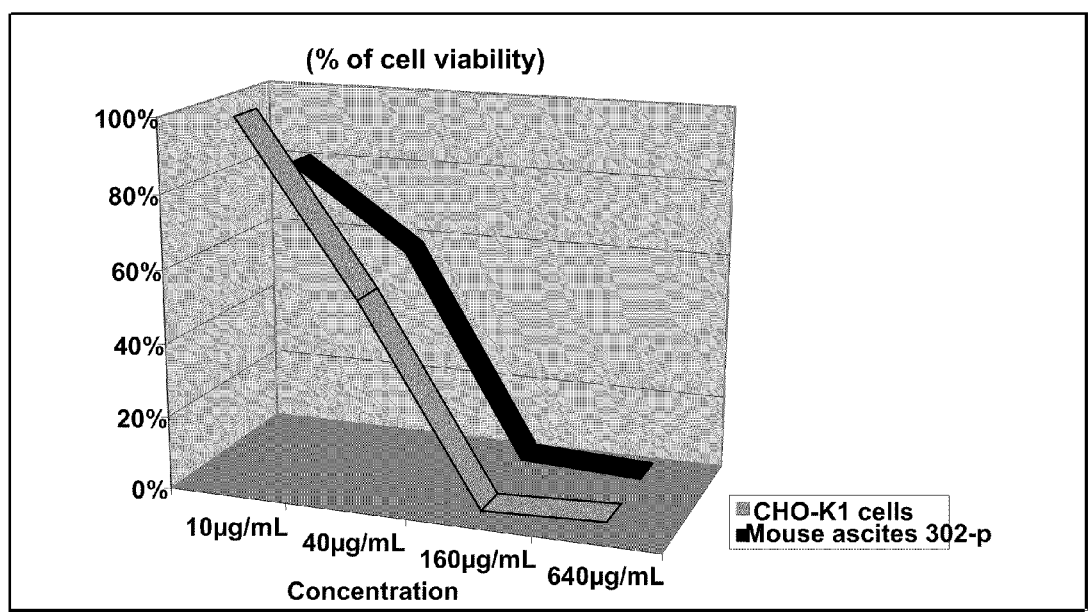
FIG. 6 shows the cytotoxicity of the NafNaf pseudopeptide at different concentrations on normal cells and cancer cells.

These are given in FIG. 6.

The cytotoxicity of the NafNaf pseudopeptide was measured on hamster cells (CHO-K1) and a mouse cell line (ascites 302-sp).

This pseudopeptide has no cytotoxic effect on the hamster cells at 10 µg/mL, a bactericidal concentration for bacterial strains such as *S. aureus* and the lethal dose for 50% of the cells ($LD_{50}$) is approximately 40 µg/mL.

These results obtained with the non-cancerous hamster cells are confirmed by the results obtained on the mouse cell line ascites 302-sp which is a cell line derived from cancer cells. The LD50 is slightly lower but there is still a slight effect on the cell viability at 10 µg/mL.

EXAMPLE 5

Measurement of the Bacterial Activity in a Rich Medium 5.1. Operating Procedure

The tests were carried out on Gram-negative bacterial strains: *Escherichia coli* ATCC 25922, *Salmonella enterica* ATCC 13076, *Pseudomonas aeruginosa* ATCC 27853, *Klebsiella oxytoca* CIP 7932, *Enterobacter aerogenes* ATCC 13048 and *Aeromonas caviae* ATCC 15468 and on Gram-positive strains: *Staphylococcus aureus* ATCC 25923, *Enterococcus faecalis* CIP 186, *Streptococcus equinus* ATCC 5623, *Listeria monocytogenes* SOR 100, *Bacillus megaterium* ATCC 10778, *Lactococcus gaviae* ATCC 43921, *Micrococcus luteus* ATCC 10240.

The bacteria ($10^5$ CFU/mL) are incubated in a TSB (Tryptic Soy Broth) rich medium with increasing concentrations of cyclopseudopeptides (0.78, 3.12, 6.25, 12.5, 25, 50, 100 µM). This test is carried out in 96-well microplates. After incubation for 48 hours at 20° C. or 37° C., the optical density of the microplates is read at 595 nm in order to evaluate the bacterial growth and determine the minimum inhibitory concentration (MIC) for each molecule tested. Each measurement is carried out in triplicate.

5.2. Results

These are given in the table of FIG. 7.

The five sequences tested proved to be active.

The five cyclopseudopeptides are able to inhibit the growth of all the Gram-positive bacteria tested (bacteria from *S. aureus* to *M. luteus* in the table of FIG. 7) for concentration values less than or equal to 50 µM (MIC≤50 µM).

On the other hand the cyclopseudopeptides appear less active on the Gram-negative bacteria (bacteria from *E. coli* to *A. caviae* in the table of FIG. 7) and one of them (Chado) moreover exhibits no activity on the Gram-negative bacteria at the concentrations tested. The sequences OctOct and Chado are composed of aza-$\beta^3$-amino acid residues bearing alkyl chains (C8 or C12) as side chains. This chemical modification thus seems to induce an antibacterial activity preferentially directed against the Gram-negative bacteria.

*A. caviae* is resistant to all the cyclopseudopeptides at the concentrations tested and the proliferation of the other five Gram-negative bacterial strains is inhibited by the NafNaf, 4 FluoNaf and Fluokill cyclopseudopeptides in the case of MIC values comprised between 12.5 and 50 µM.

As certain MIC values are less than 10 µM on bacteria which are potentially pathogenic to humans, such as *L. monocytogenes* and *S. equinus*, a therapeutic use in humans can be envisaged.

EXAMPLE 6

Measurement of the Haemolytic Activity of Different Peptides According to the Invention on Sheep Erythrocytes 6.1. Operating Procedure The haemolytic activity of the pseudopeptides is tested on sheep blood cells. The sheep erythrocytes are washed three times with a phosphate buffer saline [PBS buffer (pH 7.4)] by 5 minutes' centrifugation at 900 g and the final pellet is suspended in PBS. For the concentration of the erythrocyte solution, a concentration of erythrocytes corresponding to $OD_{540\ nm}$ is established, and for the control well 100% haemolysis in the presence of 0.8 Triton X-100. The solutions of the different pseudopeptides diluted in water (100 µL) are arranged in a 96-well plate. 50 µL of PBS 2× buffer solution then 50 µL of sheep erythrocyte solution is added to these solutions in order to produce a final volume of 200 µL. The suspensions obtained are incubated for 1 hour at 37° C. The samples are then centrifuged at 500 g for 5 min. 130 µL of supernatant of each sample is transferred to a new 96-well plate. The release of haemoglobin is quantified by measuring the absorbance at 540 nm of the supernatant by means of a microplate reader. The controls corresponding to the absence of haemolysis (white) and 100% haemolysis involve, respectively, the addition of 100 µL of PBS buffer and 100 µL of a 2% Triton X-100 solution to the wells containing 100 µL of saline erythrocyte solution (50 µL of PBS 2× and 50 µL of blood cell solution). Each measurement is carried out in triplicate.

6.2. Results

These are given in FIG. 8.

The compounds NafNaf, 4-Fluo-1-Naf, and FluoKil exhibit no significant haemolytic activity at the doses tested.

OctOct and ChaDo exhibit maximum haemolytic activity of 52% and 61% respectively at 100 µM. Nevertheless, at 12.5 µM, a concentration at which they inhibit the growth of several Gram-positive bacteria, their haemolytic activities are less, of the order of 10% in the case of OctOct and 20% in the case of Chado.

The invention claimed is:

1. A cyclic peptide having a random alternation of L-α-aminoacyl residues and aza-$β^3$-aminoacyl residues corresponding to formula (A),

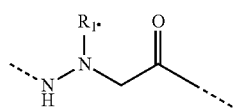

(A)

wherein,

R1 represents a proteogenic side chain, providing that,

L-α-aminoacyl residues are always separated by one aza-$β^3$-aminoacyl residue, and the total number of L-α-aminoacyl residues and aza-$β^3$-aminoacyl residues is between 4 and 8, inclusive.

2. The cyclic peptide according to claim 1, wherein the peptide is a hexapeptide or an octapeptide.

3. The cyclic peptide according to claim 1, wherein the L-α-aminoacyl residues are selected from the group consisting of: arginine, leucine, lysine, phenylalanine, serine, threonine and tryptophan.

4. The cyclic peptide according to claim 1, wherein R1 represents a side chain of natural amino acid residues or non-natural amino acid residues.

5. The cyclic peptide according to claim 4, wherein the natural amino acid residues are selected from the group consisting of: arginine, leucine, lysine, phenylalanine, serine, threonine and tryptophan residues.

6. The cyclic peptide according to claim 4, wherein the non-natural amino acid residues are selected from the group consisting of:

1-naphthylalanine [(1)Nal],
2-naphthylalanine [(2)Nal],
4-phenyl-phenylalanine (4Bip),
diphenylalanine (Dip),
9-anthracenylalanine [(9)Ath],
4-pyridylalanine [(4)Pal],
3-pyridylalanine [(3)Pal],
2-pyridylalanine [(2)Pal],
fluorophenylalanine (4-Fpa),
dodecylalanine (Amy),
nonylalanine (Non),
octylalanine (Oct),
cyclohexylalanine (Cha),
4-fluoro-1-naphthylalanine (4-F-1-Nal),
homoserine (Hse),
homo γ-hydroxythreonine, and
norleucine (Nle) residues.

7. The cyclic peptide according to claim 1, having the sequence (Ia):

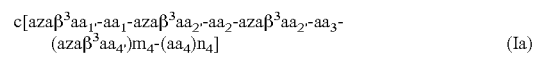

(Ia)

wherein, each of $aa_1$, $aa_2$, $aa_3$, and $aa_4$ independently represents an L-α-aminoacyl residue, each of $azaβ^3aa_{1'}$, $azaβ^3aa_{2'}$, $azaβ^3aa_{2'}$, and $azaβ^3aa_{4'}$ independently represents an aza-$β^3$-amino acid, corresponding to formula (A), and $m_4$ and $n_4$ each simultaneously represent 0 or 1.

8. The cyclic peptide according to claim 1, having the sequence (Ib):

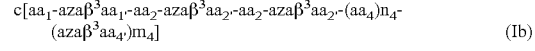

(Ib)

wherein, each of $aa_1$, $aa_2$, $aa_2$, and $aa_4$ independently represents an L-α-aminoacyl residue, each of $azaβ^3aa_{4'}$, $azaβ^3aa_{2'}$, $azaβ^3aa_{2'}$ and $azaβ^3aa_{4'}$, independently represents an aza-$β^3$-amino acid, corresponding to formula (A), and $m_4$ and $n_4$ each simultaneously represent 0 or 1.

9. The cyclic peptide according to claim 1, having the sequence (Ic):

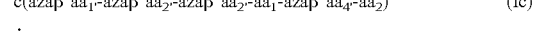

(Ic)

wherein, each of $aa_1$ and $aa_2$ independently represents an L-α-aminoacyl residue, each of $azaβ^3aa_{4'}$, $azaβ^3aa_{2'}$, $azaβ^3aa_{2'}$ and $azaβ^3aa_{4'}$ independently represents an aza-$β^3$-amino acid, corresponding to formula (A).

10. The cyclic peptide according to claim 1, having the sequence (Id):

$$c(aza\beta^3aa_{1'}\text{-}aza\beta^3aa_{2'}\text{-}aa_1\text{-}aza\beta^3aa_{1'}\text{-}aa_2) \quad (Id)$$

wherein,
each of $aa_1$ and $aa_2$ independently represents an L-α-aminoacyl residue,
each of $aza\beta^3aa_{1'}$ and $aza\beta^3aa_{2'}$ independently represents an aza-$\beta^3$-amino acid, corresponding to formula (A).

11. The cyclic peptide according to claim 7, selected from the group consisting of the following sequences:

SEQ ID NO 1: c[-Leu-*aza*β³Lys-Lys-*aza*β³(1)Nal-Leu-*aza*β³(1)Nal-] (NafNaf),

SEQ ID NO 2: c[-Lys-*aza*β³Lys-Leu-*aza*β³(1)Nal-Leu-*aza*β³(1)Nal-] (NalNal),

SEQ ID NO 3: c[-Lys-*aza*β³Lys-Trp-*aza*β³Leu-Trp-*aza*β³Leu-] (TrypTryp),

SEQ ID NO 4: c[-Lys-*aza*β³Lys-Lys-*aza*β³Leu-Trp-*aza*β³Leu-] (3KW),

SEQ ID NO 5: c[-Trp-*aza*β³Lys-Lys-*aza*β³Lys-Trp-*aza*β³Leu-] (3K2),

SEQ ID NO 6: c[-Lys-*aza*β³Lys-Lys-*aza*β³Lys-Trp-*aza*β³(1)Nal-] (4KW),

SEQ ID NO 7: c[-Ser-*aza*β³(1)Nal-Phe-*aza*β³Lys-Thr-*aza*β³Lys-Ser-*aza*β³Lys-] (SNalF), SEQ ID NO 8: c[Leu-*aza*β³Arg-Arg-*aza*β³(1)Nal-Leu-*aza*β³(1)Nal-] (RNaf), SEQ ID NO 9: c[-Leu-*aza*β³Lys-Lys-*aza*β³(1)Nal-] *aza*β³Leu-*aza*β³(1)Nal-] (Nafaza)

SEQ ID NO 10: c[-Phe-*aza*β³Lys-Lys-*aza*β³(1)Nal-Phe-*aza*β³(1)Nal-] (PheNal),

SEQ ID NO 11: c[-Leu-*aza*β³Lys-Lys-*aza*β³Leu-*aza*β³(1)Nal-] (5pNala),

SEQ ID NO 12: c[-*aza*β³Lys-Lys-*aza*β³(1)Nal-Leu-*aza*β³(1)Nal-] (5pNafa).

SEQ ID NO 13: c[-Leu-*aza*β³Lys-Lys-*aza*β³(1)-Nal-Leu-*aza*β³(4F-1)Nal-]( 4Fluo1Naf), SEQ ID NO 14: c[-Lys-*aza*β³Lys-Trp-*aza*β³Oct-Trp-*aza*β³Oct-] (OctOct), SEQ ID NO 15: c[-Lys-*aza*β³Lys-Cha-*aza*β³Amy-Trp-*aza*β³(1)Nal-] (Chado), SEQ ID NO 16: c[-Arg-*aza*β³Lys-Cha-*aza*β³(4)Fpa-Trp-*aza*β³Cha-] (FluoKil), SEQ ID NO 17: c[-Leu-*aza*β³Lys-Lys-*aza*β³(2)Nal-Leu-*aza*β³(2)Nal-] (Naf2Naf2), SEQ ID NO 18: c[-Phe-*aza*β³Lys-Arg-*aza*β³(2)Nal-Phe-*aza*β³(2)Nal-] (PheNar2), SEQ ID NO 19: c[-Leu-*aza*β³Lys-Lys-*aza*β³(1)Nal-Leu-*aza*β³(4)Fluo-(1)Nal-] (4FluoNaf), SEQ ID NO 20: c[-Leu-*aza*β³Lys-Lys-*aza*β³Bip-Leu-*aza*β³Bip-] (BipBip), SEQ ID NO 21: c[-*aza*β³Lys-Lys-*aza*β³Bip-Leu-*aza*β³Bip-] (5pBip), SEQ ID NO 22: c[-Leu-*aza*β³Arg-Arg-*aza*β³(1)Nal-Leu-] (5pRNaf), SEQ ID NO 23: c[-Leu-*aza*β³Lys-Lys-Leu-*aza*β³(1)Nal-] (5pNafaza), SEQ ID NO 24: c[-*aza*β³Lys-Arg-*aza*β³(2)Nal-Phe-*aza*β³(2)Nal-] (5pPheNar2), SEQ ID NO 25: c[-*aza*β³Lys-Lys-*aza*β³(2)Nal-Leu-*aza*β³(2)Nal-] (5pNaf2).

12. A medicament, comprising the cyclic peptide according to claim 1.

13. The medicament according to claim 12, wherein the medicament is an anti-infective agent or a disinfectant.

14. A pharmaceutical composition, comprising at least one cyclic peptide according to claim 1 combined with a pharmaceutically acceptable excipient.

15. A method of treating bacterial infections in humans or animals, comprising bringing said bacterial cells into contact with at least one cyclic peptide according to claim 1, in a quantity of said cyclic peptide sufficient to cause death of the bacterial cells without causing death of cells of said human or said animal.

* * * * *

UNITED STATES PATENT AND TRADEMARK OFFICE
CERTIFICATE OF CORRECTION

PATENT NO. : 8,603,968 B2
APPLICATION NO. : 12/682129
DATED : December 10, 2013
INVENTOR(S) : Laurencin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 731 days.

Signed and Sealed this
Twenty-second Day of September, 2015

Michelle K. Lee
*Director of the United States Patent and Trademark Office*